United States Patent
Kearney et al.

(10) Patent No.: US 10,016,524 B2
(45) Date of Patent: Jul. 10, 2018

(54) PREFABRICATED ALGINATE-DRUG BANDAGES

(71) Applicants: President and Fellows of Harvard College, Cambridge, MA (US); Beth Israel Deaconess Medical Center, Inc., Boston, MA (US)

(72) Inventors: Cathal J. Kearney, Boston, MA (US); Uyanga Tsedev, Cambridge, MA (US); David J. Mooney, Sudbury, MA (US); Aristidis Veves, Quincy, MA (US); Thomas Michael Braschler, Quincy, MA (US); Sidi A. Bencherif, Dorchester, MA (US)

(73) Assignees: President and Fellows of Harvard College, Cambridge, MA (US); Beth Israel Deaconess Medical Center, Inc., Boston, MA (US)

( * ) Notice: Subject to any disclaimer, the term of this patent is extended or adjusted under 35 U.S.C. 154(b) by 110 days.

(21) Appl. No.: 14/783,559

(22) PCT Filed: Apr. 11, 2014

(86) PCT No.: PCT/US2014/033867
§ 371 (c)(1),
(2) Date: Oct. 9, 2015

(87) PCT Pub. No.: WO2014/169250
PCT Pub. Date: Oct. 16, 2014

(65) Prior Publication Data
US 2016/0058903 A1    Mar. 3, 2016

Related U.S. Application Data

(60) Provisional application No. 61/810,854, filed on Apr. 11, 2013.

(51) Int. Cl.
| | |
|---|---|
| *A61L 15/00* | (2006.01) |
| *A61K 38/00* | (2006.01) |
| *A61L 15/28* | (2006.01) |
| *A61K 38/04* | (2006.01) |
| *A61L 15/42* | (2006.01) |
| *A61L 15/44* | (2006.01) |

(52) U.S. Cl.
CPC ............ *A61L 15/28* (2013.01); *A61K 38/046* (2013.01); *A61L 15/425* (2013.01); *A61L 15/44* (2013.01); *A61L 2300/412* (2013.01)

(58) Field of Classification Search
CPC ........ A61L 15/28; A61L 15/425; A61L 15/44; A61L 2300/412; C08L 5/04; A61K 38/046
See application file for complete search history.

(56) References Cited

U.S. PATENT DOCUMENTS

| | | | |
|---|---|---|---|
| 5,888,987 A | 3/1999 | Haynes et al. | |
| 6,334,968 B1 | 1/2002 | Shapiro et al. | |
| 2006/0141018 A1 | 6/2006 | Cochrum et al. | |
| 2007/0154448 A1* | 7/2007 | Reid | A61K 38/046 424/85.1 |
| 2008/0044900 A1* | 2/2008 | Mooney | A61L 27/3633 435/375 |
| 2009/0028834 A1* | 1/2009 | Siegel | A61K 38/08 424/93.7 |
| 2009/0075903 A1* | 3/2009 | Siegel | A61K 38/046 514/16.6 |
| 2009/0156504 A1* | 6/2009 | Siegel | A61K 38/08 514/19.4 |
| 2010/0092561 A1* | 4/2010 | Reid | A61K 38/046 424/486 |
| 2010/0143477 A1* | 6/2010 | Siegel | A61K 38/08 424/484 |
| 2012/0134967 A1* | 5/2012 | Mooney | A61L 27/3633 424/93.7 |
| 2013/0029030 A1 | 1/2013 | Larsen | |

OTHER PUBLICATIONS

Genes et al. Effect of substrate mechanics on chondrocyte adhesion to modified alginate surfaces. Arch Biochem Biophys. Feb. 15, 2004;422(2):161-7.*
Genes, et al., Effect of substrate mechanics on chondrocyte adhesion to modified alginate surfaces. Archives of biochemistry and biophysics, 422:161-167, 2004.

* cited by examiner

*Primary Examiner* — Robert A Wax
*Assistant Examiner* — Olga V Tcherkasskaya
(74) *Attorney, Agent, or Firm* — McCarter & English, LLP; Maria Laccortipe Zacharakis; Wei Song

(57) ABSTRACT

The invention provides a solution to the drawbacks associated with conventional alginate dressings. This invention features improved alginate dressings or bandages as well as a fabrication process that results in an alginate sheet that is preloaded with drug, can be stored in a freeze-dried state, and is compliant and ready to use at the time of administration.

22 Claims, 10 Drawing Sheets

PREFABRICATED ALGINATE-DRUG BANDAGES

RELATED APPLICATIONS

This application is a 35 U.S.C. § 371 national stage filing of International Application No. PCT/US2014/033867, filed Apr. 11, 2014, which in turn claims the benefit, and priority to, U.S. Provisional Application No. 61/810,854, filed Apr. 11, 2013, The contents of each of the foregoing applications are hereby incorporated herein by reference in their entirety.

GOVERNMENT SUPPORT

This invention was made with Government support under Grant No. 1R24DK091210-01A1 awarded by the NIH/NIDDK, and Grant No. 5R01EB014703-02 awarded by the NIH/NBIB. The Government has certain rights in the invention.

SEQUENCE LISTING

The instant application contains a Sequence Listing which has been submitted electronically in ASCII format and is hereby incorporated by reference in its entirety. Said ASCII copy, created on Nov. 8, 2017, is named 117823-09002 SL.txt and is 4,117 bytes in size.

FIELD OF THE INVENTION

The invention relates to wound dressings.

BACKGROUND OF THE INVENTION

Alginate dressings are wound coverings made from a polymer derived from seaweed. Such dressings maintain a moist microenvironment that promotes healing. They can be biodegradable and have been successfully used for variety of secreting lesions. The dressing limits accumulation of wound secretions and minimizes bacterial contamination.

One drawback of alginate that limits the use of alginate dressing is its fabrication process. In order to prefabricate the bandage, it is cross-linked in advance and stored at room temperature, thus making it incompatible with sensitive or labile drugs, cells, or proteins that are prone to degradation under room temperature conditions.

SUMMARY OF THE INVENTION

The invention provides a solution to the drawbacks associated with conventional alginate dressings. This invention features improved alginate dressings or bandages, e.g., a topical dressing or bandage, as well as a fabrication process that results in an alginate sheet that is preloaded with drug, can be stored in a freeze-dried state, and is compliant and ready to use at the time of administration. The method is applicable to any ionically crosslinked hydrogel composition such as alginate, chitosan, gelatin, and collagen.

Accordingly, a method of making a compliant bandage composition includes the steps of providing an alginate solution, molding said solution into a desired shape, inducing a cryo-organized structure by freezing and lyophilizing said molded solution, and contacting said cryo-organized structure with a crosslinking agent to yield a compliant bandage composition.

Preferably, the step of contacting the alginate with a crosslinking agent is carried out after the step of inducing a cryo-organized structure, e.g., by freezing and then lyophilizing. The crosslinking stabilizes or locks in place the 3-dimensional pore structure induced by freezing the mixture. The pores are interconnected. The cryo-organization of alginate resulting from the freeze-drying process confers flexibility to the composition, and the crosslinking process stabilizes the structure to maintain flexibility. Depending on the fabrication conditions, the pores are generally homogeneous, heterogeneous, and/or aligned. In some cases, a gauze fabric is added to the alginate solution prior to inducing the cryo-organized structure and then crosslinking.

The resulting composition is a compliant bandage or wound dressing and is suitable for contacting a bodily tissue (human or non-human animal) immediately. Optionally, the composition is freeze dried again for short term storage, long term storage, or for transport to a medical facility at which the product will be used. Thus, the method optionally further comprises a second freezing and lyophilizing step. If not subjected to a second freeze/dry step, the sterile gel composition can be stored for months at room temperature, at 4° C., or frozen (e.g., at −20° C. to −80° C.), the length of storage being dependent on the half-life of the incorporated drug rather than the alginate composition itself.

In preferred embodiments, the alginate solution comprises a therapeutic agent such as a drug. In one example, the agent includes a wound-healing or tissue repair compound such as substance P ("SP" or a SP-related molecule, a SP fragment, or a SP peptide derivative composition), Vascular Endothelial Growth Factor (VEGF), Platelet-Derived Growth Factor (PDGF), Stromal cell-Derived Factor (SDF), e.g., SDF-1, Epidermal Growth Factor (EGF), Transforming Growth Factor (TGF), e.g., TGF-β, Granulocyte Macrophage-Colony Stimulating Factor (GM-CSF), or Fibroblast Growth Factor (FGF). Alternatively, or in addition, the alginate contains analgesics such as ibuprofen; opiates (e.g., morphine); or topical anesthetics (e.g., benzocaine or lidocaine). Alternatively or in addition, the alginate contains and antimicrobial compound such as erythromycin, streptomycin, zithromycin, platensimycin, iodophor, 2% mupirocin, triple antibiotic ointment (TAO, bacitracin zinc+polymyxin B sulfate+neomycin sulfate) and others, as well as peptide anti-microbial agents. In some examples, the alginate comprises a hemostatic agent, e.g., microfibrillar collagen, poly-N-acetyl glucosamine, chitosan, kaolinite, thrombin, epinephrine, fibrin sealant, gelatin, mineral zeolite, aluminum chloride, silver nitrate, ferric subsulfate solution, acrylates (e.g., cyanoacrylates), ostene, bone wax, methylcellulose, glutaraldehyde, fibrinogen, or polyethylene glycol.

In some embodiments, the alginate comprises a drug to treat or alleviate a symptom of a skin/cutaneous lesion (e.g., a chronic skin lesion) or a mucous membrane lesion. Exemplary skin lesions include but are not limited to burns, eczema, psoriasis, disease wounds, acne, actinic keratosis, allergic/contact dermatitis, boils (infections that develop on hair follicles), bullae (fluid-filled sacs or lesions that appear when fluid is trapped under a layer of skin), cellulitis, chemical burns, cherry angiomas, chicken pox, cold sores, corns, calluses, cysts, dyshidrotic eczema (itchy blisters on the palms of hands and/or soles of feet), erysipelas (bacterial infections that affect the skin's upper layers), frostbite, genital herpes, gout, impetigo, insect sting allergies (e.g., mosquito bites, wasp stings), keloids (smooth, hard growths that form when scar tissue grows excessively), keratosis pilaris, lipomas, molluscum contagiosum (skin infections caused by the molluscum virus), methicillin-resistant *Staphylococcus* (Staph) infections, neurofibromas, nodules (abnormal growths that form under the skin, often filled with inflamed tissue or fluid), pemphigoid (a rare autoimmune disorder that more often affects the elderly), pemphigus vulgaris (an autoimmune disease that leads to painful blisters on skin and mucous membranes), porphyrias, scabies, scarlet fever, sebaceous cysts, seborrheic keratosis, shingles, skin cancer, warts.

Exemplary drugs that treat or alleviate a symptom (itching, raised bumps on skin, raw and sensitive skin, thicken/cracked/scaly skin, red to brownish-gray patches on skin) of eczema include corticosteroids (e.g., prednisone, methylprednisone, dexamethasone, prednisolone, or triamcinolone acetonide), antibiotics (e.g., fluoroquinolone, cephalosporins, macrocyclics, penicillins, monobactams, carbapenems, macrolides, lincosamides, streptogramins, aminioglycosides, quinolones, sulfonamides, tetracyclines, vancomycin, bacitracin, polymyxin B, or nitrofurantoin), oral antihistamines (e.g., diphenhydramine, cetirizine, fexofenadine, hydroxyzine, or loratidine), and immunomodulators (e.g., tacrolimus or pimecrolimus).

Exemplary drugs that treat or alleviate a symptom (red patches of skin covered by scales, dry cracked skin that may bleed, itching, burning, soreness, swollen or stiff joints, thickened/pitted/ridged nails) of psoriasis include hydrocortisone, prednisone, calcipotriene, mometasone, cyclosporine, adalimumab, and triamcinolone.

Exemplary drugs that treat or alleviate a symptom (e.g., pain, itchiness, infection, inflammation) of burns or disease wounds include analgesics (e.g., aspirin; non-steroidal anti-inflammatory drugs (NSAIDS) such as ibuprofen and naproxen; acetaminophen; COX-2 inhibitors such as rofecoxib, celecoxib, and etoricoxib; opiods such as morphine, codeine, oxycodone, hydrocodone, dihydromorphine, buprenorphine, tramadol; or flupirtine), hydrocortisone, antibiotics (e.g., fluoroquinolone, cephalosporins, macrocyclics, penicillins, monobactams, carbapenems, macrolides, lincosamides, streptogramins, aminioglycosides, quinolones, sulfonamides, tetracyclines, vancomycin, bacitracin, polymyxin B, or nitrofurantoin), or antihistamines (e.g., diphenhydramine, cetirizine, fexofenadine, hydroxyzine, or loratidine).

Exemplary drugs to treat or alleviate a symptom of frostbite include corticosteroids (e.g., prednisone, methylprednisone, dexamethasone, prednisolone, or triamcinolone acetonide), antibiotics (e.g., fluoroquinolone, cephalosporins, macrocyclics, penicillins, monobactams, carbapenems, macrolides, lincosamides, streptogramins, aminioglycosides, quinolones, sulfonamides, tetracyclines, vancomycin, bacitracin, polymyxin B, or nitrofurantoin), aloe vera gel/lotion/cream, analgesics (e.g., aspirin; non-steroidal anti-inflammatory drugs (NSAIDS) such as ibuprofen and naproxen; acetaminophen; COX-2 inhibitors such as rofecoxib, celecoxib, and etoricoxib; opiods such as morphine, codeine, oxycodone, hydrocodone, dihydromorphine, buprenorphine, tramadol; or flupirtine).

Exemplary drugs to treat or alleviate a symptom of genital herpes include acyclovir, famciclovir, and valacyclovir.

Exemplary drugs to treat or alleviate a symptom of acne include benzoyl peroxide, salicylic acid, topical retinoids (e.g., tretinoin, isotretinoin, adapalene, or tazarotene), antibiotics (e.g., erythromycin, clindamycin, metronidazole, doxycycline, minocycline, nadifloxacin, or dapsone), oral contraceptives.

Exemplary drugs to treat or alleviate a symptom of erysipelas include antibiotics, such as penicillins, clindamycin, or erythromycin.

Exemplary drugs to treat or alleviate a symptom of methicillin-resistant *Staphylococcus* (Staph) infections include an antibiotic described above.

Typically, a therapeutic agent such as a drug is added to the alginate solution prior to molding and/or freeze-drying.

The crosslinking agent induces ionic crosslinking. For example, the crosslinking agent comprises calcium chloride, barium chloride, magnesium chloride, or potassium chloride.

Also within the invention is the product of the above-described fabrication method, e.g., a composition comprising a cryo-organized, crosslinked alginate structure comprising a therapeutic agent, wherein the structure comprises a Young's modulus of 50 kiloPascal to 500 kiloPascal (kPa), e.g., 10 kPa-250 kPa, e.g., 10 kPa-150 kPa, at room temperature. Unlike conventional alginate structures that have been frozen, these compositions are characterized by superior strength and flexibility by virtue of the cryo-organized network that has been cross-linked to stabilize it. If the composition further comprises a gauze fabric, the entire composite structure is characterized by a Young's modulus of 100 kPa to 10,000 kPa at room temperature. The function of the gauze is to confer mechanical integrity to the ionically-crosslinked composition and typically does not affect drug delivery. The gauze fabric is typically comprised of cotton of a loose open weave, e.g., 2-3 mm mesh, but can also be comprised of other polymers such as nylon or Dacron. In some examples, the composition withstands a pressure of up to 100 kPa, e.g., up to 100 kPa, 80 kPa, 60 kPa, 40 kPa, 20 kPa, 10 kPa, or 1 kPa, either continuously or discontinuously, without collapsing or losing the integrity and/or shape of the cryo-organized, cross-linked structure. In some examples, if the composition further comprises a gauze fabric, the entire composite structure is characterized by a tensile strength of 100 kPa to 10,000 kPa (e.g., 100 kPa to 5,000 kPa, 100 kPa to 1,000 kPa, 100 kPa to 500 kPa, 250 kPa to 10,000 kPa, 250 kPa to 5,000 kPa, 250 kPa to 1,000 kPa, 500 kPa to 10,000 kPa, 500 kPa to 5,000 kPa, 500 kPa to 1,000 kPa, 1,000 kPa to 10,000 kPa, 1,000 kPa to 5,000 kPa, or 5,000 kPa to 10,000 kPa) at room temperature.

In some examples, the bandage/device of the invention maintains the moisture of the bandage/device after topical administration onto a subject. For example, the bandage/device loses less than 60%, e.g., less than 60%, 50%, 40%, 30%, 20%, 15%, 10%, 5%, 2%, 1%, or less, of the water content after administration (e.g., at least 1 hour, e.g., at least 1, 2, 3, 4, 5, 6, 7, 8, 9, 10, 12, or 24 hours, 1, 2, 3, 4, 5, 6, or 7 days, 1, 2, 3, 4, or 5 weeks, or 1, 2, 3, 4, 5, 6, 7, 8, 9, or 10 months, or more after administration) compared to prior to administration. For example, the bandage/device loses less than 60%, e.g., less than 60%, 50%, 40%, 30%, 20%, 15%, 10%, 5%, 2%, 1%, or less, of its weight or mass after administration (e.g., at least 1 hour, e.g., at least 1, 2, 3, 4, 5, 6, 7, 8, 9, 10, 12, or 24 hours, 1, 2, 3, 4, 5, 6, or 7 days, 1, 2, 3, 4, or 5 weeks, or 1, 2, 3, 4, 5, 6, 7, 8, 9, or 10 months, or more after administration) compared to prior to administration. The dimensions of the bandage or wound dressing are those typical for topically applied bandages, i.e., the size corresponds to the wound to be treated. The thickness generally comprises 0.1 mm-10 mm, e.g., 1 mm-5 mm or 1 mm-2 mm. Release of drug depends on the affinity of the drug for the network structure, e.g., alginate, as well as diffusion. Thus, a thinner gel, e.g., 1 mm-5 mm in thickness, permits more rapid release of drug to a tissue than a thicker dressing. The drug release profile associated with a thickness of 1 mm-2 mm is compatible with the customary clinical schedule of changing would dressings. For slower release, the bandage is optionally fabricated at a greater thickness, thereby retarding drug release due to the greater distance the drug must travel to exit the dressing.

The width and length of the bandage or wound dressing vary depending on the size of the wound or the use. For example, the width and/or length of the bandage or wound dressing comprises 0.5 cm-12 cm, e.g., 0.5 cm-6 cm, 0.5 cm-3 cm, 0.5 cm-2 cm, 1 cm-12 cm, 2 cm-12 cm, 3 cm-12 cm, 6 cm-12 cm, 8 cm-12 cm, 10 cm-12 cm, 2 cm-10 cm, 2 cm-8 cm, 2 cm-6 cm, or 4 cm-8 cm. For example, the surface area of the bandage or wound dressing comprises 0.2 $cm^2$-144 $cm^2$, e.g., 0.2 $cm^2$-100 $cm^2$, 0.2 $cm^2$-60 $cm^2$, 0.2 $cm^2$-30 $cm^2$, 0.2 $cm^2$-10 $cm^2$, 0.2 $cm^2$-4 $cm^2$, 1 $cm^2$-100 $cm^2$, 1 $cm^2$-60 $cm^2$, 1 $cm^2$-30 $cm^2$, 1 $cm^2$-10 $cm^2$, 5 $cm^2$-144 $cm^2$, 5 $cm^2$-100 $cm^2$, 5 $cm^2$-60 $cm^2$, 5 $cm^2$-30 $cm^2$, 25 $cm^2$-144 $cm^2$, 25 $cm^2$-100 $cm^2$, 100 $cm^2$-144 $cm^2$, 25 $cm^2$-100 $cm^2$, or 40 $cm^2$-80 $cm^2$.

The cryo-organized structure comprises a network of pores, which is formed during and after the first freeze/dry/thaw cycle. The superior physical properties of the alginate composition are due to the interconnected pores (e.g., network of gaps) that form between alginate strands as a result of the freezing step. Ice crystals form during the freezing process, and alginate concentrates around the ice crystals. The cryo-organized structure is an alginate network that is left behind after the ice/frozen water is removed by lyophilization/drying. After removal of the water by freeze/drying the mixture, the network lacks mechanical integrity. The ionic crosslinking step (using aqueous or non-aqueous ionic crosslinking agents) confers structural integrity upon the structure, while maintaining an interconnected pore structure.

As is described above, the composition contains a therapeutic agent such as an tissue repair/wound healing compound.

The device includes one or more therapeutic compositions, e.g., drugs such as proteins, peptides, small molecules, nucleic acids, or even whole cells. The compounds are purified naturally-occurring, synthetically produced, or recombinant compounds, e.g., polypeptides, nucleic acids, small molecules, or other agents. The compositions described herein are purified. Purified compounds are at least 60% by weight (dry weight) the compound of interest. Preferably, the preparation is at least 75%, more preferably at least 90%, and most preferably at least 99%, by weight the compound of interest. Purity is measured by any appropriate standard method, for example, by column chromatography, polyacrylamide gel electrophoresis, or HPLC analysis. Cells are also purified or enriched for a particular cell type or phenotype. For example, a sample of cells of a particular tissue type or phenotype is "substantially pure" when it is at least 60% of the cell population. Preferably, the preparation is at least 75%, more preferably at least 90%, and most preferably at least 99% or 100%, of the cell population. Cells are purified or enriched using a variety of known methods, e.g., selection by cell surface markers using marker-specific antibodies or other ligands. Purity is measured by any appropriate standard method, for example, by fluorescence-activated cell sorting (FACS).

The invention also features a method of promoting wound healing or tissue repair. The method includes contacting a bodily tissue such as an injured or diseased tissue of a subject with a composition, e.g., bandage/device, described herein. For example, the composition, e.g., bandage/device comprises a therapeutic agent. For example, the composition, e.g., bandage/device mediates controlled release, e.g., sustained or delayed release, of the therapeutic agent to a tissue/wound of the subject.

Exemplary therapeutic agents are described above. For example, the therapeutic agent comprises substance P.

In some embodiments, the size of a wound of the subject is reduced compared to the size of the wound prior to contacting the subject with a composition, e.g., bandage/device, described herein. For example, the size of the wound is reduced by at least 1.5-fold, e.g., at least 1.5-fold, 2-fold, 3-fold, 4-fold, 5-fold, 10-fold, 15-fold, 20-fold, 30-fold, 40-fold, 50-fold. In some examples, the size of a wound is a perimeter or area of the wound. In some cases, administration of the composition, e.g., bandage/device, results in a complete closure of a wound in the subject. For example, complete closure of the wound occurs within 6 months, e.g., within 6 months, 5 months, 4 months, 3 months, 2 months, 1 month, 5 weeks, 4 weeks, 3 weeks, 2 weeks, 1 week, 7 days, 6 days, 5 days, 4 days, 3 days, 2 days, 1 day, or less, after administration of the device/bandage.

In some embodiments, the devices/bandages of the invention are effective in treating or alleviating a symptom of a skin lesion, e.g., a chronic skin lesion. Exemplary skin lesions are described above. For example, the devices/bandages of the invention are effective in treating or alleviating a symptom of eczema, psoriasis, frostbite, bacterial infections, or burns.

In some embodiments, the device/bandage directly contacts an injured, damaged, or diseased tissue, e.g., at the site of a cutaneous/mucous membrane injury, damage, or disease (such as a skin/mucous membrane lesion or disease described above). In some cases, the device/bandage covers the site of a cutaneous/mucous membrane injury and extends to and/or overlaps onto healthy unaffected tissue, e.g., healthy unaffected skin or mucous membrane.

In some embodiments, the devices/bandages of the invention are effective in reducing pain in a subject. In some examples, the devices/bandages of the invention are effective in reducing pain in a subject by at least 5%, e.g., at least 5%, 10%, 15%, 20%, 25%, 30%, 40%, 50%, 60%, 70%, 80%, 90%, 95%, or greater, compared to the level of pain prior to administration of the device/bandage. In some cases, pain, e.g., at the site of administration, is eliminated after administration of the device/bandage.

In some embodiments, the subject comprises diabetes. For example, the subject comprises a diabetic wound, e.g., an ischemic wound. In some examples, the ischemic wound comprises a neuroischemic wound.

In some embodiments, the composition, e.g., bandage/device, of the invention is not suitable for injection into a subject.

Other features and advantages of the invention will be apparent from the following description of the preferred embodiments thereof, and from the claims. All references cited herein are incorporated by reference.

DETAILED DESCRIPTION

Figure 1:
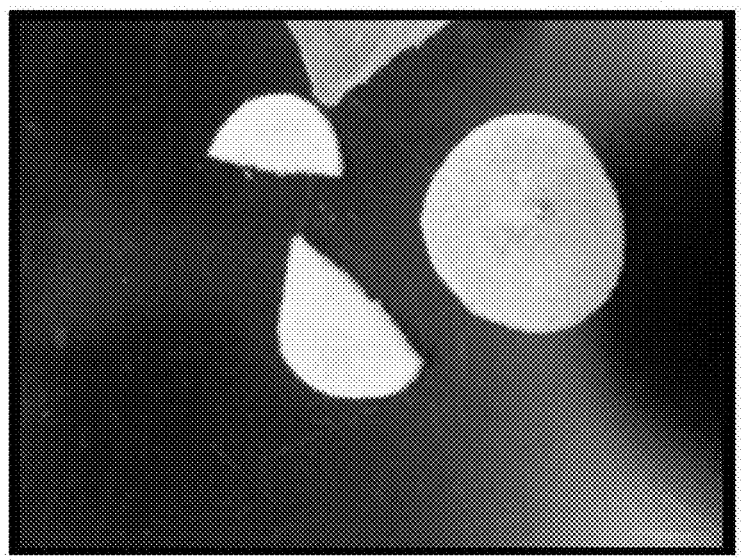
FIG. 1 is a photograph of an ionically cross-linked alginate sheet following freeze-drying, which breaks easily during handling.

Alginate has been used for scaffolds and/or cell and drug carriers. It has also been used as a non-drug delivering bandage in topical wound healing situations. The drawback of alginate for this application is its fabrication process. In order to prefabricate the bandage, it is cross-linked in advance and stored at room temperature. Such storage conditions make it incompatible with many drugs, cells, or proteins that degrade in room temperature. One way of overcoming this problem is to prepare the alginate delivery device as an injectable solution at the time of administration; however, this approach is time consuming and impractical for a surgical setting.

Described herein is a novel fabrication process that results in an alginate sheet that is preloaded with drug, can be stored in a freeze-dried state, and is compliant and ready to use at the time of administration. The device can be manufactured in a variety of sizes (e.g., ready to use sizes) and can also be easily cut to size at the time of use. The alginate sheet has a defined physical form that matches the mold in which it is manufactured. The compositions and methods are useful for a variety of payloads, i.e., compounds to be delivered to injured or diseased tissues. For example, alginate bandages have been fabricated to contain Substance P, a peptide drug. Delivery of Substance P from the bandage has efficacy in wound healing in diabetics. The alginate dressings/bandages have applicability over a large range of small molecule drugs, peptides, proteins, and cells. The alginate sheets/devices of the invention are stored, e.g., at room temperature, for long periods of time without loss of mechanical integrity, drug delivery function, or tissue protective function, e.g., at least 1 day, e.g., at least 1, 2, 3, 4, 5, 6, 7 days, 1, 2, 3, 4, 5 weeks, 1, 2, 3, 4, 5, 6, 7, 8, 9, 10, 11, 12 months, 1, 2, 3, 4, 5 years, or longer. Also, the stored alginate devices are compliant immediately upon hydration. Some previously available devices or gels containing drug(s) that are sensitive to degradation at room temperature have a short shelf life due to the instability of the drug(s). In contrast, the alginate devices/bandages of the invention permit storage of degradation-sensitive drug(s) within the devices for longer periods of time, e.g., at least 1, 2, 3, 4, 5, 6, 7 days, 1, 2, 3, 4, 5 weeks, 1, 2, 3, 4, 5, 6, 7, 8, 9, 10, 11, 12 months, 1, 2, 3, 4, 5 years, or longer, e.g., at room temperature, without degradation of the drug(s). As such, the devices are highly portable and are useful for applications such as field combat, hiking/expeditions, sailing, and use in third world countries.

In addition, the alginate dressings/bandages provide protection of wounds, e.g., open wounds and/or surgical wounds from physical force. The dressings/bandages also provide controlled (e.g., delayed or sustained) delivery of therapeutic agents (e.g., topically) without the need for any invasive procedures, e.g., without the need for implantation or injection. The hydrogel nature of the device (e.g., high water content) helps maintain moisture in the wound site, which is favorable for wound healing.

In addition, the devices/bandages can be modified to customize them for the intended use. For example, the devices/bandages can be customized for use as a wound covering that is easily removed, e.g., for cleaning or replacement. Alginate does not have any natural ligands for cells to adhere to; thus by using alginate hydrogels, the device does not become infiltrated by cells and tissue does not form in the device. In this way, the design of the bandage is such that the bandage does not become integrated with any newly formed tissue at the wound site. This property makes the device removable from the wound site, e.g., without re-damaging the wound site when the device is removed. This is unlike gauze alone, which when left on a wound too long can become enveloped by newly formed tissue—the wound site can then be damaged when the gauze is removed.

On the other hand, if the intended use is to build cells/tissue in and/or around the device, e.g., in tissue engineering, the alginate is chemically modified by attaching cell adhesion ligands to the alginate. In some examples, the alginate is chemically modified to undergo degradation (e.g., oxidation). The cell adhesion ligands, in combination with the macroporous structure of the device, then permit cell infiltration. For example, the alginate bandage is incorporated into/around the healing tissue (e.g., around or in a wound).

Alginate

Alginate is a linear polysaccharide consisting of (1,4)-linked b-D-mannuronate (M) and its C-5 epimer α-L-guluronate (G). The monomers can appear in homopolymeric blocks of consecutive G-residues (G-blocks), consecutive M-residues (M-blocks), alternating M and G-residues (MG-blocks) or randomly organized blocks. Chemical composition, primary structure and average block lengths are conveniently determined by NMR spectroscopy. Commercial alginates are generally extracted from brown algae, and the relative amount of each block type varies with the origin of the alginate. Physical-chemical and biological properties of alginate vary widely with chemical composition. G-blocks form stable cross-linked junctions with divalent cations (e.g. $Ca^{2+}$, $Ba^{2+}$, $Sr^{2+}$, among others) leading to a three-dimensional gel network. Alginate can also form gels under acidic conditions without cross-linking agents.

Fabrication Technique

Figure 4:
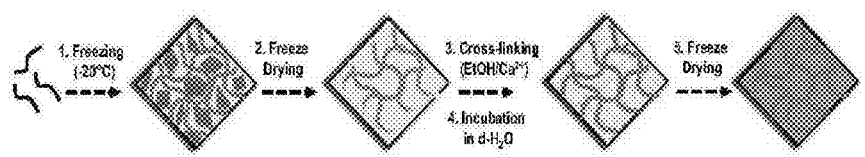
FIG. 4 is a flow diagram showing the preparation of calcium crosslinked cryo-organized alginate (COA) gels with an interconnected macrostructure. Alginate was first dissolved in water, frozen at −20° C. (1), and then freeze-dried to generate a cryo-organized macroporous architecture (2). COA was subsequently ionically calcium cross-linked (3) and re-equilibrated in water (4). COA was freeze-dried a second time for long-term storage (5).

Freeze-drying is commonly used in preparing sensitive biological agents for long-term storage as it helps reduce hydrolytic effects on them. Ionically cross-linked alginate materials, however, become extremely brittle and are difficult to handle after undergoing freeze-drying due to a propensity to break or shatter (FIG. 1). This makes it difficult for the end user to apply the bandage, while also complicating the devices storage and transport. Manufacture of the cryo-organized pore structure confers flexibility on the composition, and crosslinking after cryo-organization preserves the flexible physical property, which in part, results in compliance to pressure An alternative approach to fabricate the device (drug delivery bandage or dressing) is described herein (as described in FIGS. 2 and 4). Initially, the alginate and drug is molded into the proposed end shape of the device. For example, the device is fabricated in two forms: alginate alone or alginate in combination with gauze. The addition of gauze to the bandage increases the mechanical stiffness and strength of the device and improves handling. Afterwards, the alginate alone device or alginate+gauze device is passed through a freeze-drying process to form cryo-organized structures. A therapeutic agent is added to the alginate solution before the induction of cryo-organization (freezing) or after the lyophilization step. The terms freeze-dry and lyophilization are synonymous and used interchangeably herein. The process imparts a microstructure in the uncross-linked alginate prior to it being cross-linked. The alginate solution is chilled at the desired temperature to assure a completely frozen state. (typically at least 8 hours, e.g., overnight). Lyophilization is carried out under standard conditions, e.g., at approximately 150 millibars of pressure over a period of 1-3 days to dry the composition following freezing. For example, alginate alone (without gauze) is suitable for directly contacting a wound. In other examples, alginate contains a woven mesh (e.g., gauze) interspersed within the layer of alginate. In this case, in order to fix the alginate portion of the bandage to a wound, the alginate layer (with or without a woven mesh) is placed on the wound site (where the alginate is shaped to the size of the wound or greater). A standard wound cover (e.g., TEGADERM™) is overlaid on the alginate bandage, extending in all directions past the wound margin and attaching to the skin.

In other examples, a bandage is constructed by contacting an alginate sheet with a backing material (e.g., woven or non-woven backing material, e.g., plastic, latex, gauze, cloth, or film). Exemplary backing materials include MEPITEL™, JELONET™, OPSITE™, TEGADERM™, CARBOFLEX™, LYOFOAM C™, silicone (e.g., silicone tape), or cotton). The backing material can be porous or non-porous. For example, the backing material comprises a tape or adhesive, e.g., an adhesive plastic strip or an adhesive medical tape. For example, the contacting step is performed by gluing, fusing, spraying (e.g., spraying foam onto), or otherwise attaching the alginate sheet with the backing material. In some examples, a bandage comprises a backing material and alginate containing a woven mesh interspersed within a layer of alginate.

The presence of a backing material and/or woven mesh on or within the alginate in the bandage provides increased durability, guard against moisture loss, and protection against abrasion compared to alginate alone.

Pore size is controlled by the temperature at which the alginate solution is frozen and the rate of temperature change. Ice crystal size is dependent on the rate of freezing. The solution is frozen, e.g., by placement in a constant temperature device, at −20° C. (standard freezer), −80° C. (deep freezer), or using liquid nitrogen, e.g., −160° C., −180° C., −200° C., or any temperature in between to customize pore size (average diameter). For example, pores with 300-800 μm diameter, e.g., 500 μm diameter, are formed at −20° C.; pores with 100-400 μm diameter, e.g., 100-200 μm diameter, are formed at about −70 to −88° C.; and pores with 10-99/100 μm diameter, e.g., 50 μm diameter, are formed using liquid nitrogen, e.g., at about −180° C. The pores are interconnected and generally homogeneous throughout the alginate composition. To promote formation of homogeneous pores, the mold into which the alginate solution is poured is optionally pre-chilled/frozen prior to pouring the solution into the mold. To form heterogeneous pores, e.g., pores that are oriented or form channels, cryo-organization is induced by creating a temperature gradient. For example, a temperature gradient is created by placing the alginate solution-containing mold between 2 plates, one plate having a warmer temperature than the other plate. In this manner, ice crystal formation occurs in a single direction, e.g., from the cold surface toward the warmer surface.

During the rapid cross-linking phase a minimum volume of calcium chloride solution (100 mM) is used to crosslink the device. By rapid crosslinking phase is generally meant one hour or less, e.g., 5, 10, 15, 30, 45 minutes. Typically, crosslinking time is about 15 min. The cryo-organized alginate structure is dry (freeze-dried) prior to being contacted with the ionic crosslinking solution. Thus, the volume of crosslinking solution added to the dry composition is at least the volume of the composition and typically 1-10 times, e.g., 1-2 times, the volume of the composition (mold volume).

Figure 2:
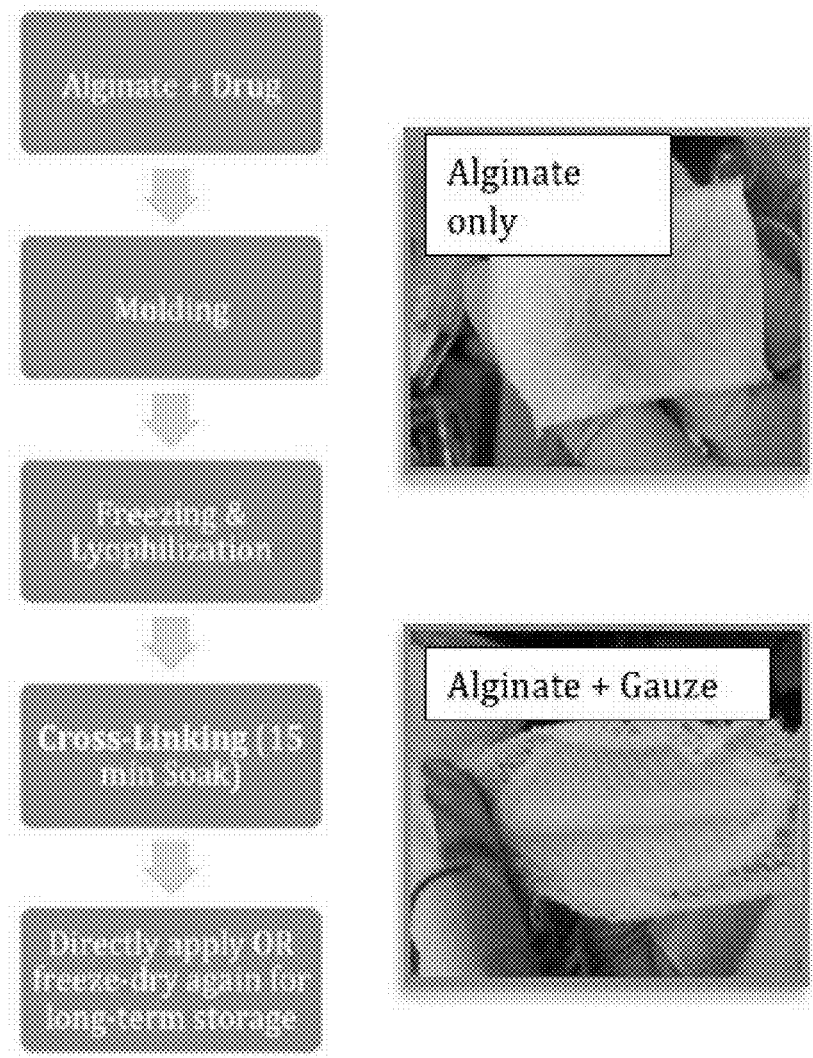
FIG. 2 is a flow diagram and set of photographs showing a fabrication process that uses an intermediary freeze-drying step to create pores in the alginate that introduce flexibility into the sheet prior to crosslinking. The starting material contains alginate+drug (optionally+gauze). Photographs of an alginate-only dressing and alginate+gauze dressing are shown in the right panel.
Figure 3:
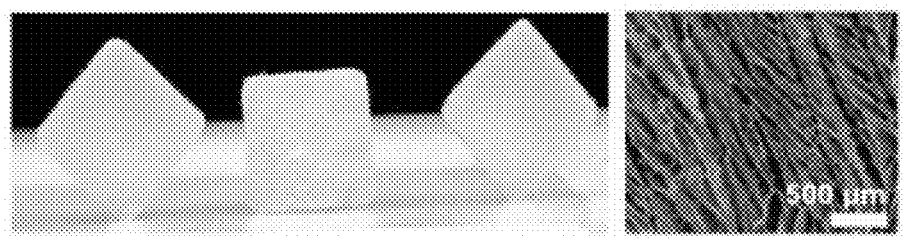
FIG. 3 are a panel of photographs. The left panel is a photograph showing freeze-dried non cross-linked cryo-organized alginate, and the right panel is a scanning electron microscope SEM image depicting a typical macroporous network structure. The network structure (comprises of pores) is generally homogenous.

The rapid crosslinking in a small volume ensures that the microstructure of freeze-drying is maintained and a minimum amount of drug is lost. FIG. 2 shows the fabrication process that uses an intermediary freeze-drying step to create micropores in the alginate that introduce flexibility into the sheet, and FIG. 3 shows a freeze-dried non cross-linked cryo-organized alginate (left) and a SEM image (right) depicting a typical macroporous network structure.

Two strategies have been used to ionically crosslink the cryo-organized alginate. First, a minimum volume of an aqueous calcium chloride solution (100 mM), e.g., calcium chloride dissolved in a physiologically acceptable buffer such as phosphate buffered saline (PBS) or HEPES buffer, was used to crosslink the device. The rapid crosslinking in a small volume ensures that the microstructure of freeze-drying is maintained and a minimum amount of drug is lost. A second method has been used to crosslink alginate in a non-aqueous solvent such as ethanol. An advantage of non-aqueous crosslinking solution is that it minimizes swelling of the alginate. As shown in FIG. 3, a macroporous cryo-organized structure can be formed after freeze-drying an aqueous solution of alginate. The lyophilized cryo-organized alginate (FIG. 4) was cross-linked in a solution of ethanol containing calcium nitrate (0.2M). Alginate being insoluble in organic solvents, especially in alcohols, the cryo-organized interconnected defined polymer structure does not get disrupted due to the lack of water, which usually leads to polymer dispersion and subsequent dissolution. Ethanol crosslinking provides a better retention and definition of the initial cryo-organized microstructure when compared to the aqueous crosslinking. Therefore, the macroporous structure is preserved during the calcium cross-linking process while entrapping molecules of drugs within the polymer walls.

There are two options for the final step with regard to the aqueously crosslinked alginate structure. In the first scenario, the device is cross-linked and applied immediately to the wound. In this case, the sterile freeze-dried alginate sheet+drugs and the sterile calcium chloride cross-linking solution are both supplied to the end user in a 'smart packaging' design that separates the alginate from the cross-linking solution until the user activates a push-and-pop mechanism (smartpack) that brings them together to permit easy cross-linking. This configuration is particularly applicable to patients with diabetic foot ulcers as they are familiar with such a system. Diabetic patients with skin/tissue ulcers such as foot ulcers already pre-wet bandages in saline before applying them, and this approach only differs in that the pre-wetting solution corresponds to the aqueous crosslinking solution, e.g., calcium chloride in water or aqueous buffer. The freeze-dried alginate bandage packaged dry, and the user contacts the dry bandage with the crosslinking solution immediately prior to applying the bandage to the skin or other tissue to be treated.

Figure 5:
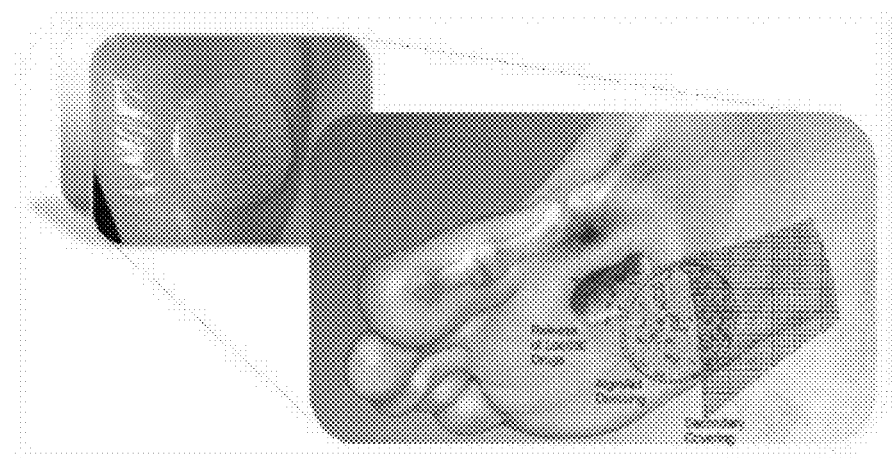
FIG. 5 is a photograph and illustration showing an alginate bandage application to a wound.

Alternatively, since the cross-linking process maintains the microstructure, it is cross-linked by the manufacturer and once again freeze-dried for long-term storage. Testing data in which the bandages underwent the dual freeze-drying process indicated that that the device maintains its desirable flexibility and mechanical properties after the second freeze-drying step. Likewise, for the ethanol cross-linking route, freeze-dried cryo-organized alginate-based drug-loaded bandages are readily provided for long-term storage or embedded in a saline solution for immediate or short-term use. The alginate bandage is applied to the skin using standard coverings, e.g., TEGADERM™. FIG. 5 shows application of alginate bandaging to a wound.

In some embodiments, the devices/bandages of the invention comprise a SP peptide, SP-related molecule, SP fragment, or SP peptide derivative composition having a particular consensus amino acid sequence. For example, the consensus amino acid sequence comprises $Xaa_1$-Pro-$Xaa_2$-Pro-$Xaa_3$-$Xaa_4$-$Xaa_5$-$Xaa_6$ (SEQ ID NO: 12). For example, $Xaa_1$ and $Xaa_2$ are positively charged amino acids, $Xaa_3$ and $Xaa_4$ are any amino acids other than Pro, and $Xaa_5$ and $Xaa_6$ are hydrophobic amino acids. $Xaa_5$ and $Xaa_6$ are preferably aromatic amino acids. For example, $Xaa_5$ and $Xaa_6$ are Phe or Trp.

In some cases, the amino acid sequence of the peptide contains at least residues 1-8 of Arg-Pro-Lys-Pro-Gln-Gln-Phe-Phe-Gly-Leu-Met (SEQ ID No: 1). In other cases, the amino acid sequence of the peptide contains at least residues 1-8 of Arg-D-Pro-Lys-Pro-Gln-Gln-D-Trp-Phe-D-Trp-Leu-Met (SEQ ID No: 2).

Other exemplary SP peptide, SP-related molecule, SP fragment, or SP peptide derivative compositions include bradykinin, Arg-Pro-Pro-Gly-Phe-Ser-Pro-Phe-Arg (SEQ ID NO: 3); neurotensin, Glu-Leu-Tyr-Glu-Asn-Lys-Pro-Arg-Arg-Pro-Tyr-Ile-Leu (SEQ ID NO: 4) or Xaa-Leu-Tyr-Glu-Asn-Lys-Pro-Arg-Arg-Pro-Tyr-Ile-Leu (SEQ ID NO: 13; where Xaa is Pyr or Tyr); indolicidin, Ile-Leu-Pro-Trp-Lys-Trp-Pro-Trp-Trp-Pro-Trp-Arg-Arg-NH2 (SEQ ID NO: 5), Lys-Pro-Arg-Pro-Gly-Gln-Phe-Phe-Gly-Leu-Met (SEQ ID NO: 6), Arg-Pro-Lys-Pro-Gln-Gln-Phe-Phe-Gly-Leu-Met (SEQ ID NO: 7), Arg-Pro-Arg-Pro-Gln-Gln-Phe-Phe-Gly-Leu-Met (SEQ ID NO: 8), Lys-Pro-Arg-Pro-Gln-Gln-Phe-Ile-Gly-Leu-Met (SEQ ID NO: 9), Lys-Pro-Arg-Pro-His-Gln-Phe-Phe-Gly-Leu-Met (SEQ ID NO: 10), or Ala-Lys-His-Asp-Lys-Phe-Tyr-Gly-Leu-Met (SEQ ID NO: 11).

In some examples, the peptide contains levorotatory (L) and/or dextrorotatory (D) forms of an amino acid. For example, the peptide has at least one D amino acid.

For example, a SP peptide, SP-related molecule, SP fragment, or SP peptide derivative composition has antimicrobial activity and contains an amino acid sequence that is at least 50% identical to the amino acid sequence of SEQ ID NO: 1. In some cases, the peptides are at least 75% identical, 85%, 95%, and 99% identical to the sequences of SEQ ID NO: 1 or 2. Nucleotide/amino acid sequence comparisons can be carried out using the Clustal W method or Clustal V method. (Higgins et al., 1989, CABIOS 5(2):151-153).

A conservative substitution of one amino acid for another is a replacement by an amino acid having a similar chemical functional side group, e.g., replacement of a positively charged amino acid by another positively charged amino acid, or replacement of a hydrophobic amino acid by another hydrophobic amino acid. The charge and hydrophobicity of amino acids is well known in the art.

In some cases, antimicrobial synthetic peptides having at least 50% identity to SP are produced by commonly known methods, such as the Merrifield solid-phase chemical synthesis method or by recombinant techniques involving the expression in cultured cells of recombinant DNA molecules encoding a gene for a desired portion of a natural or analog SP molecule. See, e.g., U.S. Pat. No. 7,723,467, the contents of which are incorporated herein by reference in its entirety.

The invention also includes synthetic SP peptide derivative compounds, which can comprise amino acid analogs such as D-amino acids, or which can be non-peptide compositions or peptide mimetics. The SP peptide derivative compounds and peptide mimetics have functional antimicrobial activity comparable to that of known SP peptides. The antimicrobial activity is for example, from about half of the activity of SP peptide, to about 2-fold, about 4-fold, or about 10-fold greater than that of SP Peptide. For example, a SP derivative is a small molecule with a molecular weight of about 100 to about 1000 Da. In other examples, a SP derivative includes analogs in which at least 1 peptide bond is replaced with an alternative type of covalent bond (a "peptide mimetic") that is resistant to cleavage by peptidases. In some examples, an L-amino acid is replaced by a D-amino acid residue; this replacement reduces the sensitivity of the compound to enzymatic destruction. In some embodiments, the SP derivative includes an amino acid analog, e.g., norleucine, norvaline, homocysteine, homoserine, or ethionine. In some cases, the SP derivative is derivatized with an amino-terminal blocking group such as a t-butyloxycarbonyl, acetyl, methyl, succinyl, methoxysuccinyl, suberyl, adipyl, azelayl, dansyl, benzyloxycarbonyl, fluorenylmethoxycarbonyl, methoxyaselayl, methoxyadipyl, methoxysuberyl, and a 2,3-dinitrophenyl group. For example, blocking the charged amino- and carboxy-termini of the peptide derived compound enhances the solubility of the compound in the hydrophobic environment of the cell membrane of the target microorganism. Such mimetics and methods of incorporating them into peptides, are well known in the art. See, e.g., U.S. Pat. No. 7,723,467, the contents of which are incorporated herein by reference in its entirety.

In some embodiments, the devices/bandages of the invention are effective in reducing pain in a subject. Measurements and scales of pain intensity are known in the art (see, e.g., Minimising pain at wound dressing-related procedures. A consensus document. London: MEP Ltd, 2004). For example, pain is quantified by the Wong-Baker FACES scale from 0-5 (where 0 indicates no pain and 5 indicates that it hurts worst); the visual analogue scale from 0-10 (where 0 indicates no pain and 10 indicates the worst pain), in which the patient is asked to pick a point on the continuum that best reflects how he/she is feeling; the numerical rating scale from 0-10 (where 0=no pain and 10=worst possible pain), in which the patient is asked to choose an integer that best places his/her current pain level; or the verbal rating scale in which the patient is asked which word best describes his/her current pain level (e.g., no pain, mild pain, moderate pain, or severe pain).

In some examples, the devices/bandages of the invention are effective in reducing pain in a subject by at least 5%, e.g., at least 5%, 10%, 15%, 20%, 25%, 30%, 40%, 50%, 60%, 70%, 80%, 90%, 95%, or greater, compared to the level of pain prior to administration of the device/bandage or is reduced by one or more units on the scale of 0-10 or 0-5 as described above. In some cases, pain, e.g., at the site of administration, is eliminated after administration of the device/bandage.

Example 1: Evaluation of Exemplary Drug Eluting Bandages

Alginate is a preferred ionically crosslinked substance from which to fabricate bandages or wound dressings due to its ability maintain moisture at the tissue site and its generally non-adhesive properties (i.e., does not stick to wounds). To demonstrate this device, a high molecular weight (HMW) medical grade alginate (ProNova Biomedical (Norway), HMW MVG alginate) was used at 2% (w/v), 4% (w/v) solution. In this example, the alginate was medium viscosity (>200 mPas) sodium alginate where minimum 60% of the monomer units are guluronate (G/M ratio≥1.5), with molecular weight of >200 kDa. Alginate for fabrication of biomaterials is well known in the art, e.g., Augst et al., 2006, Macromol Biosci 6, 623-633, see e.g., FIG. 1a; contents of publication hereby incorporated by reference. Unoxidized alginate is preferred for fabrication. For drug delivery, non-derivitized alginate, i.e., without L-arginine, glycine, and L-aspartic acid. (RGD) modification, is preferred so that the alginate does not stick to wounded or diseased tissue. For cell delivery, the alginate is optionally derivitized with RGD.

Alginate structures were made with and without an additional standard cotton gauze mesh embedded. This type of cotton gauze is used routinely in wound dressing; however, other types of gauze can be used as well. Further manipulation and enhancement of the bandage mechanical properties is accomplished through the choice of the incorporated mesh. In this example, Dynarex Conforming Stretch Sterile Gauze for testing. To embed the gauze mesh, it was placed in a mold prior to addition of the alginate. The compositions are fabricated in any desired size and shape Unless otherwise noted in this example, the bandage dimensions were 3 cm×5 cm and 2 mm thick and they were cross-linked for 15 mins in 3 ml (for 2%) or 6 ml (for 4%) of 100 mM $CaCl_2$ in a commercially available HEPES buffer.

Drug Release

The release characteristics of the test agent, Substance P (Arg-Pro-Lys-Pro-Gln-Gln-Phe-Phe-Gly-Leu-Met; RPKPQQFFGLM; SEQ ID NO: 1)), from the 2% (w/v) and 4% (w/v) bandaging sheets demonstrated its ability to retain the substance and control a sustained release of the peptide from the bandage for at least 3 days (typical duration prior to bandage change in the clinic).

Figure 6:
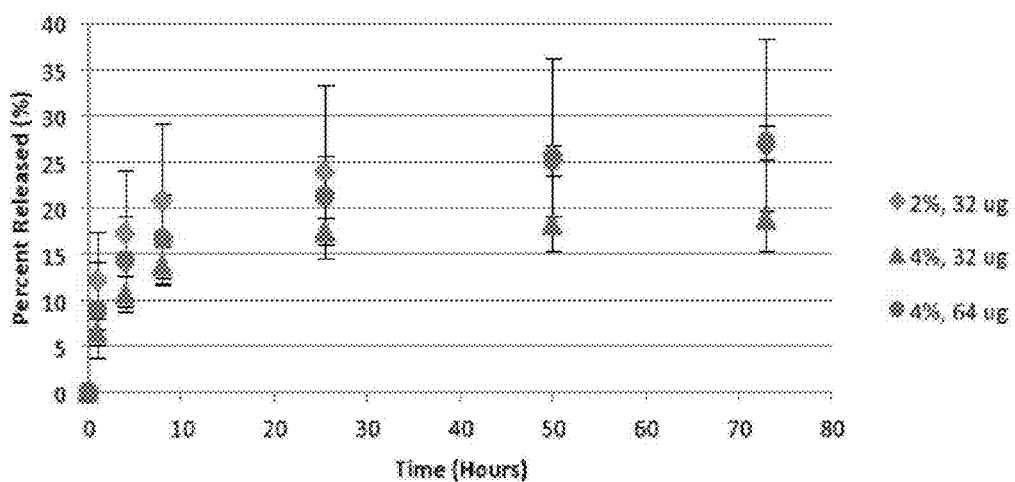
FIG. 6 is a graph and a table showing percent of Substance P (remaining after processing loss) released from the bandage material over time. The sheets incorporate either 32 µg or 64 µg of Substance P with a given processing loss (Sample size n=3 per time point).

The release was performed by placing the bandage sample of 8 mm diameter and 2 mm thickness in 2 mls of PBS and moving it to a new solution at defined time intervals. The release was examined using a commercially available ELISA assay. FIG. 6 shows the percent of Substance P (remaining after processing loss) released from the bandage material over time. The sheets incorporate either 32 μg or 64 μg of Substance P with a given processing loss (Sample size n=3 per time point). Small molecule compounds (less than 1000 daltons) are typically added to the composition in a volume of 250 al for a dressing that is about 12 mm in diameter and 2 mm thick. Thus, substance P was added at 128 μg/ml at the low concentration and 256 μg/ml at the higher concentration. Actual clinical doses are the same or similar. Since small molecules may diffuse out of the dressing quickly, it is advantageous for small molecules to have an affinity for the alginate, e.g., since alginate is negatively charged, positively charged small molecule drugs elute at a clinically acceptable and beneficial rate (and consistent with standard practice for changing of wound dressings). For example, substance P is slightly positively charged and is therefore attracted to the alginate. Charge is less or not relevant for larger molecules, e.g., BSA. Generally, the dose is determined based on the therapeutic dose of the drug. For example, VEGF is administered to the dressing at about 50 μg/ml (3 μg in 60 μl of liquid).

The data also demonstrates the ability of the bandage constituents to be adjusted to further control the release characteristics; increased drug release from the alginate material is achieved through lower sheet fiber density and/or higher drug incorporation.

Exemplary Agents

The applicability of the alginate material to the release of other types of drugs and factors was also examined. Three additional model drugs, representing classes of drugs, were tested:

1) Trypan blue dye: a small molecule that does not interact with the scaffold
2) Mitoxantrone: a cationic small molecule that interacts with the anionically charged alginate chains
3) Bovine Serum Albumin: a protein that is not subject to steric hindrance in a cross-linked alginate network, which controls its diffusion through the gel.

Figure 7:
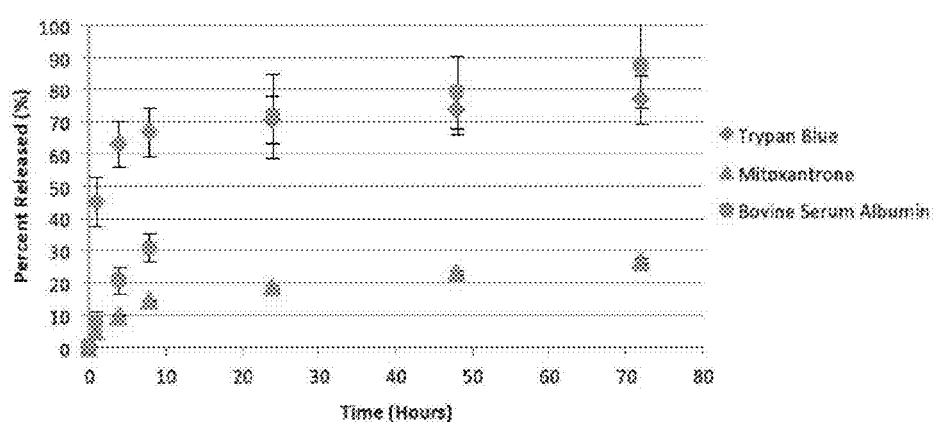
FIG. 7 is a graph and a table showing percent of Trypan Blue, Mitoxantrone, and bovine serum albumin (BSA) (remaining after processing loss) released from the bandaging material over time. (Sample size of study n=3 per time point).

Drug release was recorded for 4% (w/v) alginate pieces 8 mm in diameter and 2 mm in thickness that were crosslinked for 15 minutes. FIG. 7 shows percent of Trypan Blue, Mitoxantrone & BSA (remaining after processing loss) released from the bandaging material over time. (Sample size of study n=3 per time point).

The group of drugs differ in their affinity to the negatively charged nodes of the alginate fibers: mitoxatrone (alginate binding), trypan blue dye (negatively charged small particles easily escape the alginate structure), bovine serum albumin (negatively charged at pH 7 and hence is repelled from the alginate fibers). Their release profiles from the alginate dressing material reflect the drug—alginate interaction accordingly: the trypan is lost very rapidly (24% loss during wetting step and the majority within one day); mitoxantrone undergoes a sustained release from the scaffold, which is still ongoing at the termination of the experiment; the BSA (m.w. approximately 66.5 kDa) is repelled from the alginate scaffold, however, given its size and the density of alginate it undergoes steric hindrance and retarded diffusion from the scaffold. Taken collectively, these data demonstrate the ability of alginate to exhibit controlled release of a range of drugs from the bandage.

Mechanical Properties

Figure 8:
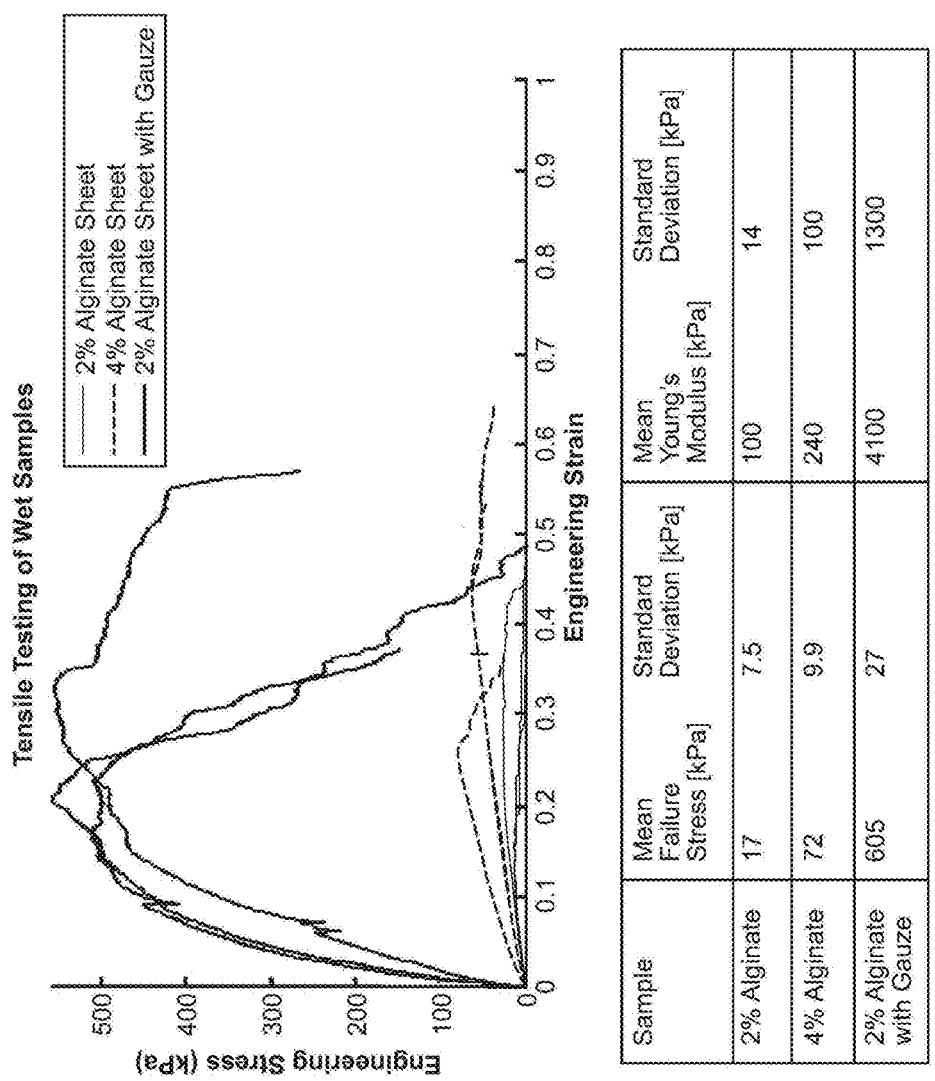
FIG. 8 is a graph and a table showing tensile properties of the bandaging material strengths with and without gauze at 2% and 4% alginate. (Sample size n=3). Mean Failure Stress is a measure of strength of the composition, and Young's Modulus is a measure of flexibility. The x-axis in the graph (Engineering Strain) represents a relative change in length of the composition when subjected to applied stress/original length of the composition.

The ability of the wetted bandages to handle the wear and tear of use is characterized by various tensile loading tests done on 2 mm thick pieces of the alginate sheets that were 12.5 mm wide and 25 mm between the grips. Engineering strength and elasticity (Young's modulus) are determined using standard methods, e.g., those described in engineering textbooks such as Ashby M F and Jones, D R H, 2011, Engineering Materials I, Fourth edition, Elsevier. FIG. 8 shows the tensile properties of the bandaging material strengths with and without gauze at 2% and 4% alginate. (Sample size n=3). These tensile properties demonstrate excellent handling potential of the dressing in clinical use, allowing for intact application and removal even at highly stressed wound areas. Based on a survey of existing bandages conducted by the inventors, 150 kPa is approximately the average failure stress of those dressings; our dressing when combine with gauze exceeds this by approximately 4-fold.

Fatigue Testing

Figure 9:
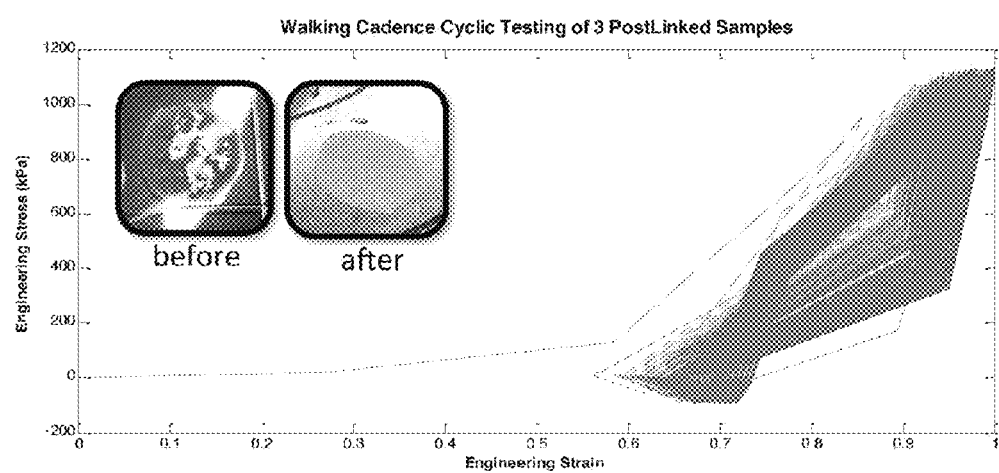
FIG. 9 is a graph of mechanical fatigue test data and a set of before and after images of the alginate bandage. The bandage dried out in the test, but stays hydrated in situ on a subject, as the environment is sealed.

To ensure that the loading from application of the bandage under a foot was well sustained by the bandage, the device was subject to cyclic compression testing. The compression cycle was constructed to imitate the loading on a foot during walking and accounted for the average daily steps taken by a diabetic subject (4000/day) for three days, with the force adjusted to available diabetic foot pressure values (1 kPa; see FIG. 9). The device survived the loading regimen, demonstrating that it was able to endure a greater number of step simulations or greater force loading with steps.

Mechanical Properties as a Function of Time

Figure 10:
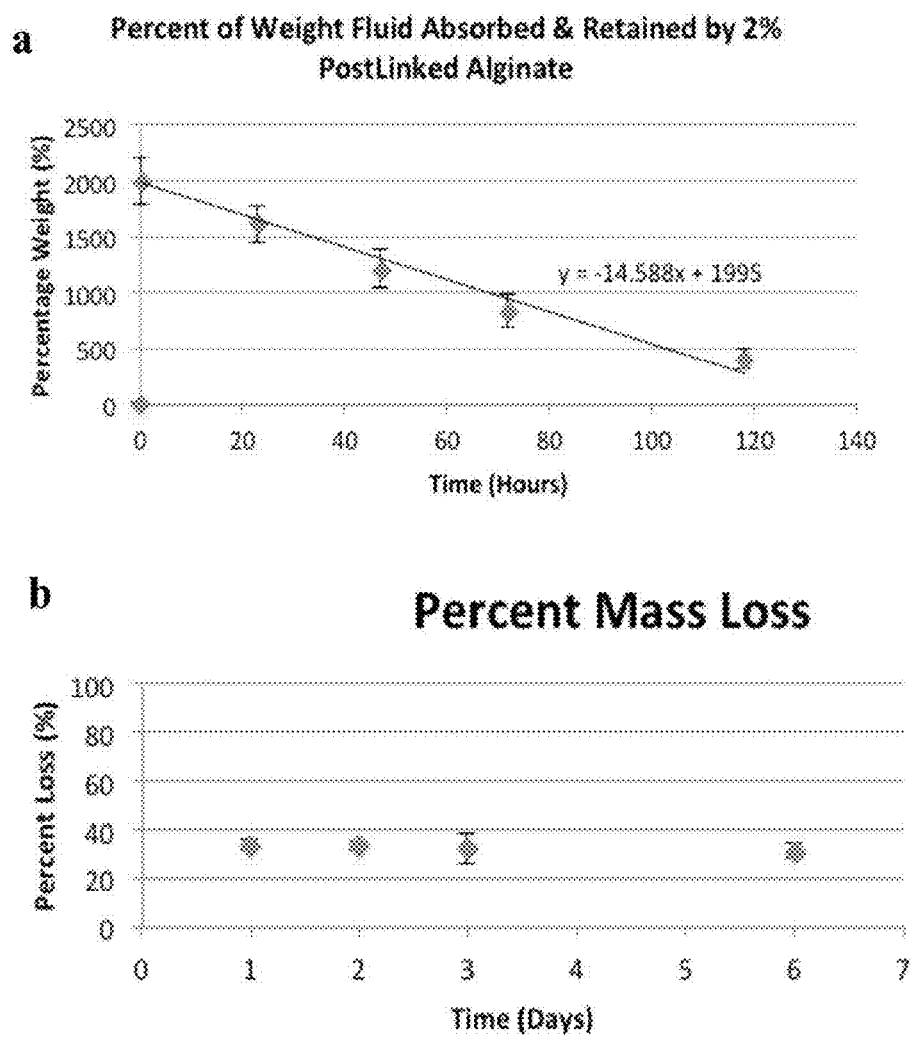
FIGS. 10A-B are a set of graphs showing the ability of devices/bandages to A) absorb and retain fluid over several days and B) resist degradation in a fluid environment. Testing was perfomed in $Ca^{2+}$ free phosphate buffered saline (PBS). As there are no natural alginate lyases in humans and as $Ca^{2+}$ is present in wound exudate, these testing conditions are good models for wound environments. Based on these results, the bandages likely perform at least this well in a wound environment.

To evaluate the ability of the device to absorb and maintain moisture, tests were conducted on a bandage of 2 mm thickness (FIG. 10). A stability test (measured by weight change) was also conducted to determine if the bandaging experienced significant degradation and loss of mechanical robustness (FIG. 10). (Note: all testing sample size n=3). At 37° C., the device was able to absorb liquid (phosphate buffered saline containing physiologic levels of calcium and magnesium) up to 20 times the weight of the alginate material itself.

The device also retained most of this moisture with loss of less than 20% of the contained liquid with each passing day (at 37° C. in non-sealed containers). In vivo, any losses may in fact be remediated by exudate absorption as well as the sealing provided by a secondary covering over the alginate dressing.

Figure 11:
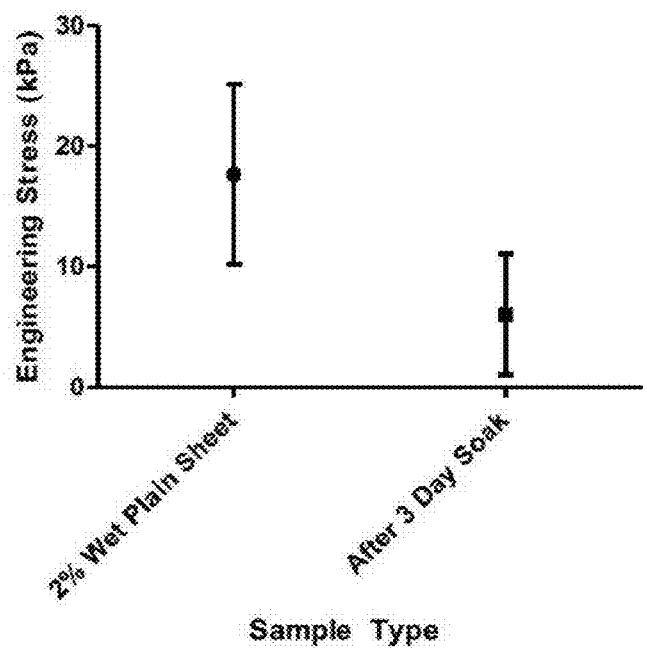
FIG. 11 shows the mechanical properties of the bandages as a function of time. The loss of calcium when the device/bandage is placed in calcium-free phosphate buffered saline (PBS) resulted in a reduction in mechanical properties, e.g., engineering stress and Young's modulus. However, calcium ions in the wound exudate prevent such a reduction in mechanical properties when the bandage is applied to a wound of a subject.
Figure 11:
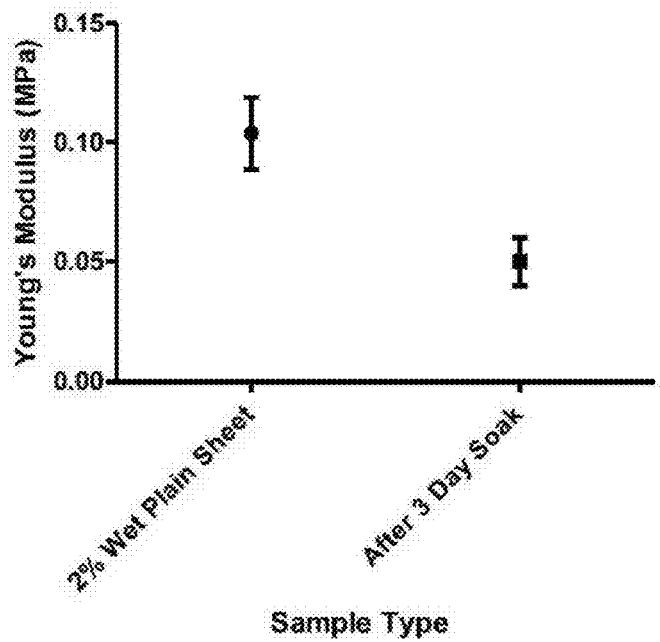

When the device was placed in a calcium free environment, there was an initial mass loss (attributed to calcium removed from the device), but afterwards the weight remained constant. The diffusion of $Ca^{2+}$ reduced the mechanical strength and Young's Modulus of the material (FIG. 11). However in vivo, calcium in the serum/exudate in the wound environment and minimizes these effects on mechanical properties of the device.

Example 2: Animal Studies

Figure 12:
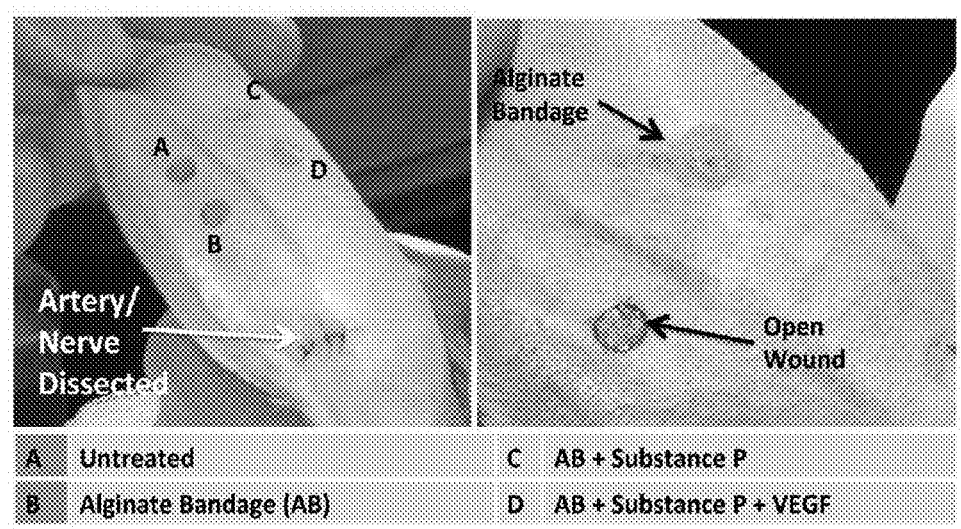
FIG. 12 is a set of photographs of a rabbit neuroischemic diabetic wound healing model showing the alginate bandage in place. The ear was subsequently covered with a standard off-the-shelf adhesive covering that is routinely used in wound care. These bandages remained in place and were easily exchanged at three days.

To test the device handling in a clinical setting, a rabbit study was performed with two rabbits. Diabetes was induced in the rabbits using alloxan and their blood glucose monitored and controlled. The central auricular artery and nerve were isolated and cut (neuroischemia) or left intact (sham). Four full thickness skin wounds were then created using a biopsy punch, and when bleeding had ceased, the wounds were filled with the prefabricated alginate bandages as shown in FIG. 12.

The reports back from the surgeons and animal care staff regarding the ability of the bandage to be applied, to stay in place, and to be easily removed were positive.

Example 3: Rabbit Ear Wound Healing Model

Experiments are performed to test the efficacy of the bandage in a neuroischemic and a neuroischemic+diabetes rabbit ear wound healing model using known methods, e.g., those described in Pradhan et al., J. Vasc. Surg. 2013, 58(3): 766-775, incorporated herein by reference. The bandages are tested alone; with Substance-P alone (32 μg); with VEGF alone (3 μg); or with a combination of VEGF and Substance-P. Bandages are exchanged every 3 days (a typical timeframe for cleaning) and the wound area examined at 10 days for % percent healing and histological analysis.

The described alginate sheet material hence has numerous applications as a wound dressing that maintains moist and non-traumatic healing environment and deliver therapeutic elements in a controlled manner. A highly absorptive alginate bandage with good handling properties that can control release of select drugs was developed utilizing a medical grade alginate, e.g., alginate that has FDA approval in other applications, and a standard gauze material. The fabrication process described herein yields a strong, flexible, cross-linked alginate product that is superior to conventional alginate bandages or dressings.

OTHER EMBODIMENTS

The patent and scientific literature referred to herein establishes the knowledge that is available to those with skill in the art. All United States patents and published or unpublished United States patent applications cited herein are incorporated by reference. All published foreign patents and patent applications cited herein are hereby incorporated by reference. All other published references, documents, manuscripts and scientific literature cited herein are hereby incorporated by reference.

While this invention has been particularly shown and described with references to preferred embodiments thereof, it will be understood by those skilled in the art that various changes in form and details may be made therein without departing from the scope of the invention encompassed by the appended claims.

We claim:

1. A composition comprising a cryo-organized, cross-linked alginate structure comprising a therapeutic agent and a woven mesh, wherein said composition comprises a Young's modulus of 100 kiloPascals to 10,000 kiloPascals at room temperature.

2. The composition of claim 1, wherein said cryo-organized structure comprises a network of interconnected cross-linked pores.

3. The composition of claim 1, wherein said therapeutic agent comprises substance P.

4. A method of promoting wound healing or tissue repair, comprising contacting a tissue of a subject with the composition of claim 1.

5. The method of claim 4, wherein said therapeutic agent comprises substance P.

6. The method of claim 4, wherein the wound is a diabetic wound.

7. The method of claim 6, wherein the diabetic wound comprises an ischemic wound.

8. The composition of claim 1, wherein said structure comprises a Young's modulus of to 1,000 kiloPascals to 10,000 kiloPascals at room temperature.

9. The composition of claim 1, wherein said structure comprises a Young's modulus of 1,000 kiloPascals to 5,000 kiloPascals at room temperature.

10. The composition of claim 1, wherein the thickness of said composition is 0.1 mm-10 mm.

11. The composition of claim 1, wherein said alginate comprises non-oxidized alginate.

12. The composition of claim 1, wherein said alginate comprises oxidized alginate.

13. The composition of claim 1, wherein said therapeutic agent is a wound-healing or tissue repair compound.

14. The composition of claim 13, wherein said therapeutic agent is selected from the group consisting of substance P, Vascular Endothelial Growth Factor, Platelet-Derived Growth Factor, Stromal cell-Derived Factor, Epidermal Growth Factor, Transforming Growth Factor, Granulocyte Macrophage-Colony Stimulating Factor, and Fibroblast Growth Factor.

15. The composition of claim 3, wherein said substance P is selected from the group consisting of a SP peptide, a SP-related molecule, a SP fragment, and a SP peptide derivative.

16. The composition of claim 15, wherein said substance P comprises:
   (i) an amino acid sequence that is at least 50% identical to the amino acid sequence of SEQ ID NO: 1 or 2;
   (ii) an amino acid sequence that is at least residues 1-8 of SEQ ID NO: 1 or 2;
   (iii) the amino acid sequence of SEQ ID NO: 1;
   (iv) the amino acid sequence of SEQ ID NO: 2; or
   (v) a consensus amino acid sequence, wherein the consensus amino acid sequence comprises $Xaa_1$-Pro-$Xaa_2$-Pro-$Xaa_3$-$Xaa_4$-$Xaa_5$-$Xaa_6$ (SEQ ID NO: 12).

17. The composition of claim 2, wherein said pores have a diameter of 10 μm-100 μm, 100 μm-200 μm, 100 μm-400 μm, or 300 μm-800 μm.

18. The composition of claim 17, wherein the alginate is crosslinked ionically.

19. The composition of claim 1, wherein said woven mesh is a gauze.

20. The composition of claim 1, wherein said woven mesh is interspersed within the alginate structure.

21. The composition of claim 1, further comprising a backing material.

22. The composition of claim 1, further comprising a cell.

* * * * *

UNITED STATES PATENT AND TRADEMARK OFFICE
CERTIFICATE OF CORRECTION

PATENT NO.       : 10,016,524 B2
APPLICATION NO.  : 14/783559
DATED            : July 10, 2018
INVENTOR(S)      : Kearney et al.

Page 1 of 1

It is certified that error appears in the above-identified patent and that said Letters Patent is hereby corrected as shown below:

In the Claims

Column 24, Claim 17, Line 7, insert -- 10 μm - 800 μm, -- in front of "10 μm - 100 μm".

Signed and Sealed this
Fourth Day of September, 2018

Andrei Iancu
*Director of the United States Patent and Trademark Office*

SEQUENCE LISTING

<160> NUMBER OF SEQ ID NOS: 13

<210> SEQ ID NO 1
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1

Arg Pro Lys Pro Gln Gln Phe Phe Gly Leu Met
1               5                   10

<210> SEQ ID NO 2
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: D-amino acid
<220> FEATURE:
<221> NAME/KEY: MOD_RES
<222> LOCATION: (7)..(7)
<223> OTHER INFORMATION: D-amino acid
<220> FEATURE:
<221> NAME/KEY: MOD_RES
<222> LOCATION: (9)..(9)
<223> OTHER INFORMATION: D-amino acid

<400> SEQUENCE: 2

Arg Pro Lys Pro Gln Gln Trp Phe Trp Leu Met
1               5                   10

<210> SEQ ID NO 3
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 3

Arg Pro Pro Gly Phe Ser Pro Phe Arg
1               5

<210> SEQ ID NO 4
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 4

Glu Leu Tyr Glu Asn Lys Pro Arg Arg Pro Tyr Ile Leu
1               5                   10

<210> SEQ ID NO 5
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:

```
<223> OTHER INFORMATION: C-term NH2

<400> SEQUENCE: 5

Ile Leu Pro Trp Lys Trp Pro Trp Trp Pro Trp Arg Arg
1               5                   10

<210> SEQ ID NO 6
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 6

Lys Pro Arg Pro Gly Gln Phe Phe Gly Leu Met
1               5                   10

<210> SEQ ID NO 7
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 7

Arg Pro Lys Pro Gln Gln Phe Phe Gly Leu Met
1               5                   10

<210> SEQ ID NO 8
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 8

Arg Pro Arg Pro Gln Gln Phe Phe Gly Leu Met
1               5                   10

<210> SEQ ID NO 9
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 9

Lys Pro Arg Pro Gln Gln Phe Ile Gly Leu Met
1               5                   10

<210> SEQ ID NO 10
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 10

Lys Pro Arg Pro His Gln Phe Phe Gly Leu Met
1               5                   10

<210> SEQ ID NO 11
```

```
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 11

Ala Lys His Asp Lys Phe Tyr Gly Leu Met
1               5                   10

<210> SEQ ID NO 12
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Any positively charged amino acid
<220> FEATURE:
<221> NAME/KEY: MOD_RES
<222> LOCATION: (3)..(3)
<223> OTHER INFORMATION: Any positively charged amino acid
<220> FEATURE:
<221> NAME/KEY: MOD_RES
<222> LOCATION: (5)..(6)
<223> OTHER INFORMATION: Any amino acid other than Pro
<220> FEATURE:
<221> NAME/KEY: MOD_RES
<222> LOCATION: (7)..(8)
<223> OTHER INFORMATION: Any hydrophobic amino acid

<400> SEQUENCE: 12

Xaa Pro Xaa Pro Xaa Xaa Xaa Xaa
1               5

<210> SEQ ID NO 13
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Pyr or Tyr

<400> SEQUENCE: 13

Xaa Leu Tyr Glu Asn Lys Pro Arg Arg Pro Tyr Ile Leu
1               5                   10
```